United States Patent [19]

Kuzemchak

[11] Patent Number: 4,692,159
[45] Date of Patent: Sep. 8, 1987

[54] OSTOMY POUCH FLUSH NOZZLE

[76] Inventor: James J. Kuzemchak, P.O. Box 741, Indiana, Pa. 15701

[21] Appl. No.: 917,303

[22] Filed: Oct. 9, 1986

Related U.S. Application Data

[63] Continuation of Ser. No. 773,294, Sep. 6, 1985, abandoned.

[51] Int. Cl.⁴ .................................................. A61M 31/00
[52] U.S. Cl. ...................................... 604/277; 604/344
[58] Field of Search .............. 604/267, 276, 277, 334; 285/DIG. 22, 345, 331; 239/567, 559, 288, 288.5, 272

[56] References Cited

U.S. PATENT DOCUMENTS

| | | | |
|---|---|---|---|
| 3,913,845 | 10/1975 | Tsuji | 239/556 |
| 4,050,461 | 9/1977 | Ruby | 604/277 |
| 4,491,271 | 1/1985 | Hasenack | 239/567 |

Primary Examiner—C. Fred Rosenbaum
Assistant Examiner—J. L. Kruter
Attorney, Agent, or Firm—Larson and Taylor

[57] ABSTRACT

A flushing device for an ostomy bag is disclosed which comprises an adapter designed to fit in the ringed opening of an ostomy bag and having an internally threaded opening capable of receiving and forming a water-tight seal with a male-threaded water nozzle from a hose. The device is comprised of a circular plastic disk having a base flange and a cylindrical adapter projecting from the base flange including a forward circular flange positioned at the front end of the adapter at a distance from the base flange substantially the same as the width of the ring surrounding the opening of the ostomy bag. The flushing device enables the user to flush out an ostomy bag safely and effectively without mess or backspray.

3 Claims, 7 Drawing Figures

OSTOMY POUCH FLUSH NOZZLE

This application is a continuation of application Ser. No. 773,294 filed Sept. 6, 1985, now abandoned.

FIELD OF THE INVENTION

The present invention relates to an adapter which is used to allow cleaning of a ostomy bag.

BACKGROUND OF THE INVENTION

With the recent rise in the number of instances of colon cancer, there has also been an increase in the total number of people undergoing colostomies. A colostomy is a surgical procedure by which a new opening, or stoma, is provided in the front of the abdomen to allow the discharge of feces from the body. In order to collect this waste material, a bag or pouch is continuously worn by the colostomy patient. Once these bags fill up, it is necessary to empty them and, if reusable, wash them out. This task has not been performed quickly and efficiently with a minimum of pain or inconvenience for the colostomy patient.

Previous methods used to clean out ostomy bags have not allowed quick, efficient, or thorough flushing of waste material. One such attempt is described in Voorhies U.S. Pat. No. 4,194,506. The Voorhies apparatus includes a water flushing appliance and a tube which directs water into the colostomy bag in order to flush it out. This kit operates while the bag is still attached to the patient, making it difficult for one to position himself directly over the commode for flushing. Further, cleaning of the bag while attached to the patient can be both uncomfortable and painful, as there is great pressure applied to the sensitive opening in the body of the patient. Ideally, it is desirable to have a system by which a ostomy bag can be cleaned safely, efficiently, and without undue harm or discomfort to the colostomy patient.

SUMMARY OF THE INVENTION

The problems encountered in flushing out ostomy bags and the like are greatly alleviated by the adapter of the present invention. The invention consists of an adapter which is designed to fit perfectly in the opening of the ostomy bag, and is internally threaded to receive the male end of an ordinary garden hose, or any other similar water conduit, with or without a spraying head attached. In one embodiment of the invention, the adapter comprises a circular disk with a front lip at the forward end of a diameter corresponding to the diameter of the bag opening. This forward lip, placed on a circular ring on the disk or on a central circular projection of the disk, allows for a water-tight attachment between the water source and the ostomy bag, which enables the user to flush out the bag safely and effectively without mess or backspray.

In another embodiment of the present invention, the adapter is a solid circular disk with a tapered front end. This front end can be placed inside the opening in the ostomy bag and pushed forward until the rear end of the adapter forms a water-tight seal with the bag opening. As in the previous embodiment, the adapter has central internal threads to allow a garden hose or similar conduit to be received, and an opening to allow the water to be directed into the ostomy bag.

Other features and advantages of the present invention are stated in or apparent from the detailed description of the preferred embodiments of the invention below.

DETAILED DESCRIPTION OF THE PRESENT INVENTION

Figure 1:
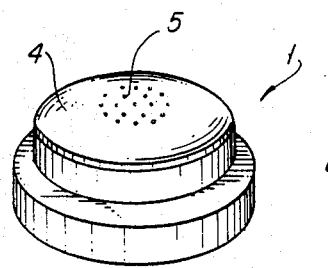
FIG. 1 is a perspective view of one embodiment of the adapter of the present invention.

Referring now more specifically to the drawings wherein like numerals refer to like parts throughout the several views there is shown at 1 in FIG. 1 an adapter specifically designed for use in flushing a ostomy bag.

Figure 4:
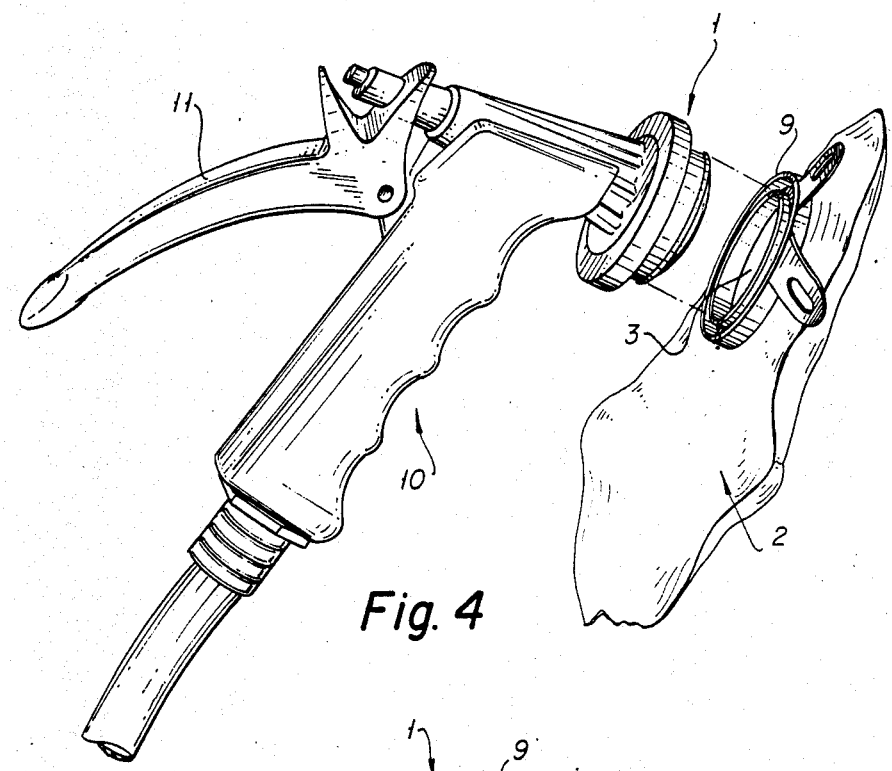
FIG. 4 is a perspective view of the adapter of the present invention positioned on the spray head of a garden hose and in a position to be attached to a ostomy bag.

The ostomy bag is shown at 2 in FIG. 4 and is provided with an opening 3 at the upper end thereof. The lower end of the bag is provided with a drainage opening which may be closed by a clip (not shown). In use the ostomy bag is attached to the patient with the opening 3 in leak proof fitting with the stoma or opening in the abdomen of the patient. When the bag is filled with feces the bag is detached from the stoma and the adapter 1 is fitted into the opening 3. The clip is removed from the drainage opening and water from a hose attached to the adapter is flushed through the bag into the commode. The bag may then be disconnected from the adapter and reattached to the stoma for subsequent use.

Figure 2:
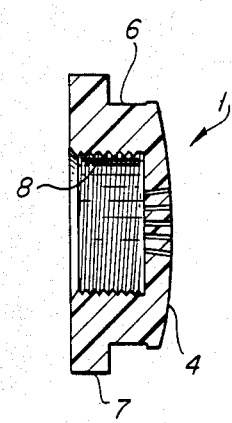
FIG. 2 is a side view, partially cut away, of the adapter of FIG. 1.
Figure 3:
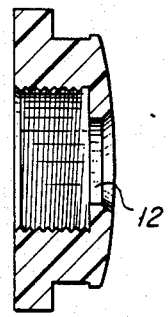
FIG. 3 is a side view of the adapter of FIG. 1, with one large central opening for the passage of water.

The adapter 1 as shown in FIGS. 1 to 3 comprises a circular disc having a locking head 4 with a plurality of openings 5 therein. As seen in FIG. 2 the locking head 4 is of slightly greater diameter than the intermediate portion 6 of the adapter. The base flange 7 is of larger diameter than both the head 4 and intermediate portion 6 of the adapter. The adapter has an internal threaded bore 8.

As seen in FIG. 4 the opening 3 in the ostomy bag is surrounded by a U-shaped flexible ring 9 which is of a width equal to the width of the intermediate portion 6 of the adapter. The inner diameter of the ring 9 is slightly smaller than the diameter of the intermediate portion 6 of the adapter.

Figure 5:
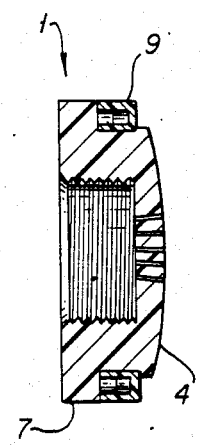
FIG. 5 is a side view of the adapter attached to the flexible ring of a ostomy bag.

In use the adapter is pressed against the ring 9. The slightly enlarged locking head 4 forces the flexible ring 9 to expand slightly as the adapter moves into the opening 3. The locking head 4 snaps into position inside the ring 9 with the inner peripheral surface of the ring surrounding the outer face of the intermediate portion 6 of the adapter 1 and in leak tight relationship therewith as seen in FIG. 5. The front face of the base flange 7 is in abutting relationship with both peripheral edges of the U-shaped ring 9. Thus, the ring 9 is gripped firmly between the locking head 4 and the base flange 7 of the adapter so that leakage or accidental removal of the adapter from the ostomy bag cannot occur.

As seen in FIG. 4 the adapter 1 may be connected to the nozzle of a conventional spray head 10 of a garden hose. This spray head may be connected by way of a hose to a water faucet so that by actuation of the lever 11 water will pass through the adapter 1 and openings 5 into the ostomy bag. The contents of the bag may be flushed out through the drainage opening in the bottom of the bag after the closure clip is removed.

Figure 6:
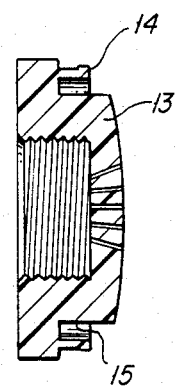
FIG. 6 is a side view of a second embodiment of the invention.
Figure 7:
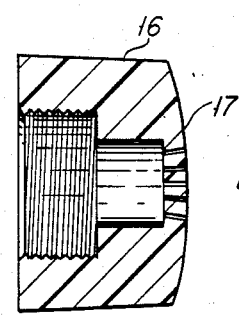
FIG. 7 is a side view of a third embodiment of the invention.

It is preferable that the openings 5 be positioned so that the outermost of the holes are slanted away from the center of the disk, as observed in FIGS. 2, 6 and 7. This enables water to be sprayed into the attached ostomy bag at all different angles, which further assists the flushing of the bag.

If desired, the adapter can also be formed with a single opening instead of the series of openings discussed above. In FIG. 3 there is shown an adapter which is identical to the adapter shown in FIGS. 1 and 2 except that a single opening 12 is provided in place of the plurality of openings 5 shown in the FIG. 1 embodiment.

In FIG. 6 there is shown an adapter 13 which is provided with an upstanding circular flange 14. This flange is adapted to be received within the arms of the U-shaped ring 9 with the outer surface 15 of the head of the adapter in tight fitting relationship with the inner surface of the ring 9.

In FIG. 7 still another embodiment of the adapter 1 is shown. In this adapter the outer surface 16 of the head is tapered inwardly toward the apertured front face 17 so that the adapter is forced within the ring 9 in the opening in the ostomy bag until a leak proof fitting is achieved between the bag and adapter.

Although the adapters are shown in FIGS. 6 and 7 with a series of openings similar to that observed in the FIG. 1 embodiment, it is also possible to construct these adapters with the single central opening observed in FIG. 3.

The adapters of the present invention are constructed of plastic or synthetic resinous materials.

Obviously many modifications and variations of the present invention are possible in light of the foregoing teachings.

What is claimed as new and is desired to be secured by Letters Patent is:

1. A flushing device for a ostomy bag wherein the ostomy bag has an opening therein and a flexible annular ring having walls forming a U-shaped cross-section surrounding the opening in the bag extending outwardly away from said bag of a predetermined width, said flushing device comprising a circular plastic disk means, said disk means having a rear face and front face and comprises:

a base flange extending from the rear face of said disk means, a cylindrical adaptor extending from said base flange and being smaller in diameter than said base flange and slightly larger in diameter than the inner diameter of the U-shaped flexible annular ring at the opening of said ostomy bag, said cylindrical projection including a forward circular flange slightly larger in diameter than said cylindrical projection and smaller in diameter than said base flange, said forward lip positioned at the front end of said cylindrical projection at a distance from said base flange substantially the same as said width of said flexible annular ring surrounding the opening of said ostomy bag, said disk means having an enlarged opening therein extending from the rear face thereof through the base flange and said cylindrical projection and terminating at the inner surface of said front face of said disk means, said enlarged opening having internal thread means therein for receiving and forming a water-tight seal with a male-threaded water nozzle from a hose, at least one opening through the the front face of said disk means whereby when said disk means is attached to a hose and the front face is forced into the opening with the U-shaped annular ring surrounding the opening of said ostomy bag, said cylindrical projection between said base flange and said forward lip fits inside the opening within the walls forming said U-shaped flexible ring to retain the ring between said lip and base flange, so that the ring is firmly retained in water tight arrangement to enable the ostomy bag to be flushed without leakage.

2. A flushing device as claimed in claim 1 wherein said forward circular flange is sized to fit openings of one inch in diameter to four inches in diameter.

3. A flushing device as claimed in claim 1 wherein said opening in the front face of said disk means comprises a plurality of small holes grouped in a circular pattern, the outermost ring of said holes being slanted away from the center of the disk, to allow water flowing through the disk to be sprayed into said ostomy bag at a plurality of different angles.

* * * * *